US008118861B2

(12) United States Patent
Hegg et al.

(10) Patent No.: US 8,118,861 B2
(45) Date of Patent: Feb. 21, 2012

(54) BIFURCATION STENT AND BALLOON ASSEMBLIES

(75) Inventors: Jens Hegg, Minneapolis, MN (US); Michael P. Meyer, Richfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 438 days.

(21) Appl. No.: 11/692,735

(22) Filed: Mar. 28, 2007

(65) Prior Publication Data
US 2008/0243232 A1 Oct. 2, 2008

(51) Int. Cl.
*A61F 2/06* (2006.01)
(52) U.S. Cl. .................. 623/1.35; 623/1.16
(58) Field of Classification Search ............ 623/1.11, 623/1.15, 1.35, 1.36, 1.37, 1.16
See application file for complete search history.

(56) References Cited

U.S. PATENT DOCUMENTS

| | | | |
|---|---|---|---|
| 4,309,994 A | 1/1982 | Grunwald | 128/214 R |
| 4,769,005 A | 9/1988 | Ginsburg et al. | 604/53 |
| 4,774,949 A | 10/1988 | Fogarty | 128/348.1 |
| 4,896,670 A | 1/1990 | Crittenden | 606/194 |
| 4,905,667 A | 3/1990 | Foerster et al. | 128/4 |
| 4,994,071 A | 2/1991 | MacGregor | 606/194 |
| 5,342,387 A | 8/1994 | Summers | 606/198 |
| 5,387,235 A | 2/1995 | Chuter | 623/1 |
| 5,456,712 A | 10/1995 | Maginot | 623/1 |
| 5,476,471 A | 12/1995 | Shifrin et al. | 606/151 |
| 5,487,730 A | 1/1996 | Marcadis et al. | 604/96 |
| 5,591,228 A | 1/1997 | Edoga | 623/1 |
| 5,607,444 A | 3/1997 | Lam | 606/194 |
| 5,609,605 A | 3/1997 | Marshall et al. | 606/191 |
| 5,609,627 A | 3/1997 | Goicoechea et al. | 623/1 |
| 5,613,980 A | 3/1997 | Chauhan | 606/194 |
| 5,617,878 A | 4/1997 | Taheri | 128/898 |
| 5,632,762 A | 5/1997 | Myler | 606/194 |
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |

(Continued)

FOREIGN PATENT DOCUMENTS
CA 2220864 7/1999
(Continued)

OTHER PUBLICATIONS

Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).

(Continued)

*Primary Examiner* — Thomas J Sweet
*Assistant Examiner* — Seema Swaminathan
(74) *Attorney, Agent, or Firm* — Vidas, Arrett & Steinkraus

(57) ABSTRACT

A bifurcated stent that is positionable adjacent to a branched body vessel. The stent includes a tapered middle portion with a side branch assembly for positioning within the deviating branch of a body vessel. The portion of the stent positioned within the first body vessel and the portion positioned within the main branch vessel have largely different sized diameters. The middle region tapers steeply to bridge this diameter differential. The tapered middle region also angles the side branch assembly which can easily be extended at an angle to the main body of the stent.

15 Claims, 9 Drawing Sheets

U.S. PATENT DOCUMENTS

| | | | | |
|---|---|---|---|---|
| 5,697,971 | A | 12/1997 | Fischell et al. | 623/1 |
| 5,707,348 | A | 1/1998 | Krogh | 602/41 |
| 5,709,713 | A | 1/1998 | Evans et al. | 623/1 |
| 5,718,724 | A | 2/1998 | Goicoechea et al. | |
| 5,720,735 | A | 2/1998 | Dorros | 604/284 |
| 5,749,825 | A | 5/1998 | Fischell et al. | 600/3 |
| 5,749,890 | A | 5/1998 | Shaknovich | 606/198 |
| 5,755,734 | A | 5/1998 | Richter et al. | 606/194 |
| 5,755,735 | A | 5/1998 | Richter et al. | 606/194 |
| 5,755,771 | A | 5/1998 | Penn et al. | 623/1 |
| 5,755,773 | A | 5/1998 | Evans et al. | 623/1 |
| 5,755,778 | A | 5/1998 | Kleshinski | 623/1 |
| 5,782,906 | A | 7/1998 | Marshall et al. | 623/1 |
| 5,800,520 | A | 9/1998 | Fogarty et al. | |
| 5,824,036 | A | 10/1998 | Lauterjung | 623/1 |
| 5,824,040 | A | 10/1998 | Cox et al. | 623/1 |
| 5,827,320 | A | 10/1998 | Richter et al. | 606/194 |
| 5,851,464 | A | 12/1998 | Davila et al. | 264/103 |
| 5,868,777 | A | 2/1999 | Lam | 606/194 |
| 5,893,887 | A | 4/1999 | Jayaraman | 623/1 |
| 5,906,640 | A | 5/1999 | Penn et al. | |
| 5,961,548 | A | 10/1999 | Shmulewitz | 623/1 |
| 5,972,017 | A | 10/1999 | Berg et al. | 606/198 |
| 6,013,054 | A | 1/2000 | Jiun Yan | 604/96 |
| 6,013,091 | A | 1/2000 | Ley et al. | |
| 6,017,324 | A | 1/2000 | Tu et al. | 604/96 |
| 6,017,363 | A | 1/2000 | Hojeibane | 623/1 |
| 6,030,414 | A | 2/2000 | Taheri | 623/1 |
| 6,033,433 | A | 3/2000 | Ehr et al. | |
| 6,033,434 | A | 3/2000 | Borghi | 623/1 |
| 6,033,435 | A | 3/2000 | Penn et al. | 623/1 |
| 6,048,361 | A | 4/2000 | Von Oepen | |
| 6,056,775 | A | 5/2000 | Borghi et al. | 623/1.16 |
| 6,059,824 | A | 5/2000 | Taheri | 623/1 |
| 6,068,655 | A | 5/2000 | Seguin et al. | 623/1 |
| 6,086,611 | A | 7/2000 | Duffy et al. | 623/1 |
| 6,093,203 | A | 7/2000 | Uflacker | 612/1.12 |
| 6,096,073 | A | 8/2000 | Webster et al. | 623/1.16 |
| 6,099,497 | A | 8/2000 | Adams et al. | 604/96.01 |
| 6,113,579 | A | 9/2000 | Eidenschink et al. | 604/264 |
| 6,117,117 | A | 9/2000 | Mauch | 604/284 |
| 6,117,156 | A | 9/2000 | Richter et al. | 606/194 |
| 6,129,738 | A | 10/2000 | Lashinski et al. | 606/194 |
| 6,129,754 | A | 10/2000 | Kanesaka et al. | |
| 6,142,973 | A | 11/2000 | Carleton et al. | 604/96 |
| 6,143,002 | A | 11/2000 | Vietmeier | 606/108 |
| 6,159,238 | A | 12/2000 | Killion et al. | 612/1.11 |
| 6,165,195 | A | 12/2000 | Wilson et al. | 606/194 |
| 6,168,621 | B1 | 1/2001 | Vrba | 623/1.2 |
| 6,183,509 | B1 | 2/2001 | Dibie | 623/1.35 |
| 6,203,568 | B1 | 3/2001 | Lombardi et al. | 623/1.13 |
| 6,210,380 | B1 | 4/2001 | Mauch | 604/284 |
| 6,210,429 | B1 | 4/2001 | Vardi et al. | 623/1.11 |
| 6,210,433 | B1 | 4/2001 | Larre | 623/1.15 |
| 6,254,593 | B1 | 7/2001 | Wilson | 606/1.11 |
| 6,258,115 | B1 | 7/2001 | Dubrul | 606/200 |
| 6,258,116 | B1 | 7/2001 | Hojeibane | 623/1.16 |
| 6,261,305 | B1 | 7/2001 | Marotta et al. | 606/200 |
| 6,261,316 | B1 | 7/2001 | Shaolian et al. | 623/1.11 |
| 6,264,662 | B1 | 7/2001 | Lauterjung | 606/108 |
| 6,264,686 | B1 | 7/2001 | Rieu et al. | 623/1.16 |
| 6,290,673 | B1 | 9/2001 | Shanley | 604/102.02 |
| 6,293,968 | B1 | 9/2001 | Taheri | 623/1.15 |
| 6,325,822 | B1 | 12/2001 | Chouinard et al. | 623/1.35 |
| 6,325,826 | B1 | 12/2001 | Vardi et al. | 623/1.35 |
| 6,334,864 | B1 | 1/2002 | Amplatz et al. | 606/200 |
| 6,346,089 | B1 | 2/2002 | Dibie | 603/1.15 |
| 6,355,060 | B1 | 3/2002 | Lenker et al. | 623/1.34 |
| 6,361,544 | B1 | 3/2002 | Wilson et al. | 606/194 |
| 6,361,555 | B1 | 3/2002 | Wilson | 623/1.11 |
| 6,383,213 | B2 | 5/2002 | Wilson et al. | 623/1.11 |
| 6,395,018 | B1 | 5/2002 | Castaneda | 623/1.13 |
| 6,436,104 | B2 | 8/2002 | Hojeibane | 606/108 |
| 6,436,134 | B2 | 8/2002 | Richter et al. | 623/1.15 |
| 6,508,836 | B2 | 1/2003 | Wilson et al. | 623/1.35 |
| 6,517,558 | B2 | 2/2003 | Gittings et al. | 606/153 |
| 6,520,988 | B1 | 2/2003 | Colombo et al. | 623/1.35 |
| 6,540,779 | B2 | 4/2003 | Richter et al. | 623/1.35 |
| 6,579,309 | B1 | 6/2003 | Loos et al. | 623/1.16 |
| 6,579,312 | B2 | 6/2003 | Wilson et al. | 623/1.35 |
| 6,582,394 | B1 | 6/2003 | Reiss et al. | 604/96.01 |
| 6,596,020 | B2 | 7/2003 | Vardi et al. | 623/1.11 |
| 6,599,316 | B2 | 7/2003 | Vardi et al. | 623/1.15 |
| 6,645,242 | B1 | 11/2003 | Quinn | 623/1.16 |
| 6,689,156 | B1 | 2/2004 | Davidson et al. | 623/1.11 |
| 6,692,483 | B2 | 2/2004 | Vardi et al. | 604/529 |
| 6,695,877 | B2 | 2/2004 | Brucker et al. | 623/1.16 |
| 6,706,062 | B2 | 3/2004 | Vardi et al. | 623/1.15 |
| 6,713,119 | B2 | 3/2004 | Hossainy et al. | |
| 6,749,628 | B1 | 6/2004 | Cho et al. | 623/1.15 |
| 6,776,793 | B2 | 8/2004 | Brown et al. | 623/1.15 |
| 6,790,228 | B2 | 9/2004 | Hossainy et al. | |
| 6,811,566 | B1 | 11/2004 | Penn et al. | 623/1.15 |
| 6,835,203 | B1 | 12/2004 | Vardi et al. | 623/1.34 |
| 6,858,038 | B2 | 2/2005 | Heuser | 623/1.35 |
| 6,884,258 | B2 | 4/2005 | Vardi et al. | 623/1.11 |
| 6,896,699 | B2 | 5/2005 | Wilson et al. | 623/1.35 |
| 6,932,837 | B2 | 8/2005 | Amplatz et al. | 623/1.15 |
| 6,955,687 | B2 | 10/2005 | Richter et al. | 623/1.35 |
| 6,955,688 | B2 | 10/2005 | Wilson et al. | 623/1.35 |
| 6,962,602 | B2 | 11/2005 | Vardi et al. | 623/1.11 |
| 7,018,400 | B2 | 3/2006 | Lashinski et al. | 623/1.11 |
| 7,041,130 | B2 | 5/2006 | Santini, Jr. et al. | |
| 7,056,323 | B2 | 6/2006 | Mareiro et al. | 606/108 |
| 7,060,091 | B2 | 6/2006 | Killion et al. | 623/1.15 |
| 2001/0003161 | A1 | 6/2001 | Vardi et al. | 623/1.11 |
| 2001/0004706 | A1 | 6/2001 | Hojeibane | 623/1.11 |
| 2001/0004707 | A1 | 6/2001 | Dereurne et al. | 623/1.16 |
| 2001/0012927 | A1 | 8/2001 | Mauch | 604/284 |
| 2001/0016766 | A1 | 8/2001 | Vardi et al. | 623/1.11 |
| 2001/0016767 | A1 | 8/2001 | Wilson et al. | 623/1.11 |
| 2001/0016768 | A1 | 8/2001 | Wilson et al. | 623/1.11 |
| 2001/0025195 | A1 | 9/2001 | Shaolian et al. | 623/1.13 |
| 2001/0027291 | A1 | 10/2001 | Shanley | 604/104 |
| 2001/0027338 | A1 | 10/2001 | Greenberg | 623/1.13 |
| 2001/0029396 | A1 | 10/2001 | Wilson et al. | 623/1.11 |
| 2001/0037116 | A1 | 11/2001 | Wilson et al. | 606/108 |
| 2001/0037138 | A1 | 11/2001 | Wilson et al. | 623/1.11 |
| 2001/0039448 | A1 | 11/2001 | Dibie | 623/1.16 |
| 2001/0049552 | A1 | 12/2001 | Richter et al. | 623/1.15 |
| 2001/0056297 | A1 | 12/2001 | Hojeibane | 623/1.16 |
| 2002/0013618 | A1 | 1/2002 | Marotta et al. | 623/1.15 |
| 2002/0013619 | A1 | 1/2002 | Shanley | 623/1.15 |
| 2002/0022874 | A1 | 2/2002 | Wilson | 623/1.11 |
| 2002/0026232 | A1 | 2/2002 | Marotta et al. | 623/1.16 |
| 2002/0035392 | A1 | 3/2002 | Wilson | 623/1.11 |
| 2002/0042650 | A1 | 4/2002 | Vardi et al. | 623/1.35 |
| 2002/0052648 | A1 | 5/2002 | McGuckin, Jr. et al. | 623/1.35 |
| 2002/0072790 | A1 | 6/2002 | McGuckin, Jr. et al. | 623/1.12 |
| 2002/0111675 | A1 | 8/2002 | Wilson | 623/1.35 |
| 2002/0156516 | A1 | 10/2002 | Vardi et al. | 623/1.11 |
| 2002/0156517 | A1 | 10/2002 | Perouse | 623/1.11 |
| 2002/0165604 | A1 | 11/2002 | Shanley | 623/1.15 |
| 2002/0173835 | A1 | 11/2002 | Bourang et al. | 623/1.11 |
| 2002/0173840 | A1 | 11/2002 | Brucker et al. | 623/1.16 |
| 2002/0183763 | A1 | 12/2002 | Callol et al. | 606/108 |
| 2002/0193872 | A1 | 12/2002 | Trout, III et al. | 623/1.34 |
| 2002/0193873 | A1 | 12/2002 | Brucker et al. | 623/1.35 |
| 2003/0009209 | A1 | 1/2003 | Hojeibane | 623/1.11 |
| 2003/0028233 | A1 | 2/2003 | Vardi et al. | 623/1.11 |
| 2003/0050688 | A1 | 3/2003 | Fischell et al. | 623/1.15 |
| 2003/0055378 | A1 | 3/2003 | Wang et al. | 604/103.07 |
| 2003/0055483 | A1 | 3/2003 | Gumm | 623/1.11 |
| 2003/0074047 | A1 | 4/2003 | Richter | 623/1.11 |
| 2003/0093109 | A1 | 5/2003 | Mauch | 606/194 |
| 2003/0097169 | A1 | 5/2003 | Brucker et al. | 623/1.11 |
| 2003/0114912 | A1 | 6/2003 | Sequin et al. | 623/1.11 |
| 2003/0125791 | A1 | 7/2003 | Sequin et al. | 623/1.11 |
| 2003/0125802 | A1 | 7/2003 | Callol et al. | 623/1.35 |
| 2003/0135259 | A1 | 7/2003 | Simso | 623/1.12 |
| 2003/0181923 | A1 | 9/2003 | Vardi | 606/108 |
| 2003/0195606 | A1 | 10/2003 | Davidson et al. | 623/1.11 |
| 2004/0006381 | A1 | 1/2004 | Sequin et al. | 623/1.12 |
| 2004/0015227 | A1 | 1/2004 | Vardi et al. | 623/1.16 |
| 2004/0044396 | A1 | 3/2004 | Clerc et al. | 623/1.13 |
| 2004/0054403 | A1 | 3/2004 | Israel | |
| 2004/0059406 | A1 | 3/2004 | Cully et al. | 623/1.11 |

| | | | | | | |
|---|---|---|---|---|---|---|
| 2004/0088007 A1 | 5/2004 | Eidenschink | 607/1 | WO | 98/19628 | 5/1998 |
| 2004/0117003 A1 | 6/2004 | Ouriel et al. | 623/1.35 | WO | 98/36709 | 8/1998 |
| 2004/0133268 A1 | 7/2004 | Davidson et al. | 623/1.35 | WO | 98/37833 | 9/1998 |
| 2004/0138732 A1 | 7/2004 | Suhr et al. | 623/1.11 | WO | 98/47447 | 10/1998 |
| 2004/0138737 A1 | 7/2004 | Davidson et al. | | WO | 98/48879 | 11/1998 |
| 2004/0148006 A1 | 7/2004 | Davidson et al. | 623/1.11 | WO | 98/53759 | 12/1998 |
| 2004/0172121 A1 | 9/2004 | Eidenschink et al. | 623/1.11 | WO | 99/03426 | 1/1999 |
| 2004/0186560 A1 | 9/2004 | Alt | 623/1.35 | WO | 99/04726 | 2/1999 |
| 2004/0204750 A1 | 10/2004 | Dinh | | WO | 99/15103 | 4/1999 |
| 2004/0225345 A1 | 11/2004 | Fischell et al. | 623/1.11 | WO | 99/15109 | 4/1999 |
| 2004/0267352 A1* | 12/2004 | Davidson et al. | 623/1.15 | WO | 99/24104 | 5/1999 |
| 2005/0004656 A1 | 1/2005 | Das | 623/1.16 | WO | 99/34749 | 7/1999 |
| 2005/0010278 A1 | 1/2005 | Vardi et al. | 623/1.35 | WO | 99/36002 | 7/1999 |
| 2005/0015108 A1 | 1/2005 | Williams et al. | 606/194 | WO | 99/36015 | 7/1999 |
| 2005/0015135 A1 | 1/2005 | Shanley | 623/1.11 | WO | 99/44539 | 9/1999 |
| 2005/0060027 A1 | 3/2005 | Khenansho et al. | 623/1.15 | WO | 99/56661 | 11/1999 |
| 2005/0096726 A1 | 5/2005 | Sequin et al. | 623/1.12 | WO | 99/65419 | 12/1999 |
| 2005/0102021 A1 | 5/2005 | Osborne | 623/1.13 | WO | 00/07523 | 2/2000 |
| 2005/0102023 A1 | 5/2005 | Yadin et al. | 623/1.15 | WO | 00/10489 | 3/2000 |
| 2005/0119731 A1 | 6/2005 | Brucker et al. | 623/1.35 | WO | 00/16719 | 3/2000 |
| 2005/0125076 A1 | 6/2005 | Ginn | 623/23.65 | WO | 00/27307 | 5/2000 |
| 2005/0131526 A1 | 6/2005 | Wong | 623/1.15 | WO | 00/27463 | 5/2000 |
| 2005/0149161 A1 | 7/2005 | Eidenschink et al. | 623/1.11 | WO | 00/28922 | 5/2000 |
| 2005/0154442 A1 | 7/2005 | Eidenschink et al. | 623/1.11 | WO | 01/45594 | 6/2000 |
| 2005/0154444 A1 | 7/2005 | Quadri | 623/1.13 | WO | 00/44307 | 8/2000 |
| 2005/0183259 A1 | 8/2005 | Eidenschink et al. | 29/508 | WO | 00/44309 | 8/2000 |
| 2005/0209673 A1 | 9/2005 | Shaked | 623/1.11 | WO | 00/47134 | 8/2000 |
| 2005/0228483 A1 | 10/2005 | Kaplan et al. | 623/1.15 | WO | 00/48531 | 8/2000 |
| 2006/0036315 A1 | 2/2006 | Yadin et al. | 623/1.35 | WO | 00/49951 | 8/2000 |
| 2006/0041303 A1 | 2/2006 | Israel | 623/1.11 | WO | 00/51523 | 9/2000 |
| 2006/0079956 A1 | 4/2006 | Eigler et al. | 623/1.35 | WO | 00/57813 | 10/2000 |
| 2006/0173528 A1 | 8/2006 | Feld et al. | 623/1.15 | WO | 00/67673 | 11/2000 |
| 2007/0073376 A1 | 3/2007 | Krolik et al. | 623/1.11 | WO | 00/71054 | 11/2000 |
| 2008/0172123 A1* | 7/2008 | Yadin | 623/1.35 | WO | 00/71055 | 11/2000 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| EP | 0479730 | 10/1991 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 00/74595 | 12/2000 |
| WO | 01/21095 | 3/2001 |
| WO | 01/21109 | 3/2001 |
| WO | 01/21244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |
| WO | 2007/139630 | 12/2007 |

OTHER PUBLICATIONS

Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).

Caputo, Ronald P., "Stent Jail: A Minimum-Security Prison," *The American Journal of Cardiology*, vol. 77, pp. 1226-1230 (Jun. 1, 1996).

Colombo, M.D., Antonio, ""Kissing" Stent for Bifurcational Coronary Lesion," *Catheterization and Cardiovascular Diagnosis*, vol. 30, pp. 327-330 (Dec. 1993).

Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).

Katoh, M.D., Osamu, "New Double Wire Technique to Stent Ostial Lesions," *Catheterization and Cardiovascular Diagnosis*, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).

Yamashita, M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).

Satler, M.D., Lowell F., "Bifurcation Disease: To Treat or Not to Treat," *Catheterization and Cardiovascular Interventions*, vol. 50, pp. 411-412 (2000).

U.S. Appl. No. 09/663,111, filed Sep. 15, 2000, Davidson et al.

U.S. Appl. No. 09/614,472, filed Jul. 11, 2000, Davidson et al.

U.S. Appl. No. 09/235,996, filed Jun. 4, 1999, Vardi et al.

\* cited by examiner

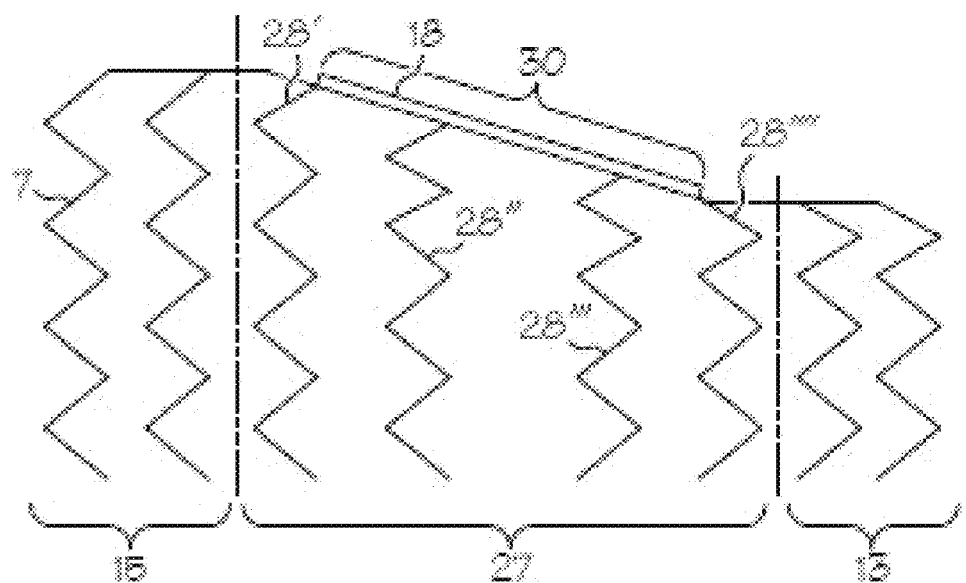

BIFURCATION STENT AND BALLOON ASSEMBLIES

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use and more particularly to intravascular stents that include a plurality of cavities formed on one or more surfaces of the stent and are coated with drugs 2. Description of the Related Art Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable). Stents may be implanted to prevent restenosis following angioplasty in the vascular system.

A complication arises when stenoses form at vessel bifurcation sites. A bifurcation site is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In one aspect of the present invention provides a bifurcated intravascular stent with a geometry that provides for a rapid decrease in the diameter of the main branch vessel relative to the diameter of the parent vessel. The stent includes a tapered middle portion with a side branch assembly for positioning within the deviating branch of a body vessel. The portion of the stent within the first body vessel and the portion within the main branch vessel have largely different sized diameters. The middle region tapers steeply to bridge this diameter differential. The tapered middle region also angles the side branch assembly which can easily be extended at an angle to the main body of the stent.

At least one embodiment of the invention is directed to a bifurcated stent having a distal region distal to the side opening and having a diameter, a proximal region proximal to the side opening and having a diameter, and a medial region between the distal and proximal regions. The stent also has a second body comprising at least one projecting member. When the stent is in the expanded state, the distal region diameter and proximal region diameter have different sizes and the medial region tapers from the distal region diameter size to the proximal region diameter size. In at least one embodiment, the difference in the diameter sizes ranges from 18% to 35% inclusively. The at least one projecting member extends obliquely from the first body and defines a second lumen therethrough, and the second lumen is in fluid communication with the first lumen. A therapeutic agent coating can be positioned on at least one connector, stent member, projecting member, the distal region, the proximal region, the medial region, the first stent body, the second stent body, and any combination thereof.

At least one embodiment of the invention is directed to a bifurcated stent in which the medial region comprises a plurality of interconnected expansion columns, at least two of the interconnected expansion columns having different maximum expansion capacities. In one embodiment the plurality can be four columns. In one embodiment a portion of the medial region extends along a sloped path between the proximal and distal regions and a portion of the medial region extending along a non-sloped linear path. The proximal and distal regions can also be tapered.

At least one embodiment is directed to a bifurcated stent in which the opening plane and a portion of the first stent body in the proximal region intersect at less than 145 degrees and/or the opening plane and a portion of the first stent body in the distal region intersect at greater than 145 degrees. In at least one embodiment, a portion of the distal region and at least a portion of the proximal region have a common axis.

At least one embodiment of the invention is directed to a bifurcated stent having at least one expandable frame which at least partially defines the perimeter of the side opening. At least one of the at least one projecting members is engaged to the expandable frame. In the unexpanded state the expandable frame has an at least partially looped structure with one or more curved regions. The curved regions at least partially extends within the opening plane to define the side opening perimeter. In the expanded state the curved regions at least partially straighten increasing the overall circumference of the side opening area. This expandable frame can also increases the overall area of the opening plane along an axis generally co-linear to an axis extending from the most distal portion of the proximal region, through the opening plane, to the most proximal portion of the distal region. This and other aspects of the invention are described in more detail in the accompanying description and drawings.

BRIEF DESCRIPTION OF THE SEVERAL VIEWS OF THE DRAWINGS

The invention is best understood from the following detailed description when read in connection with accompanying drawings, in which:

FIG. 2 is a lateral view of the medial region of a bifurcated stent.

DETAILED DESCRIPTION OF THE INVENTION

Figure 1:
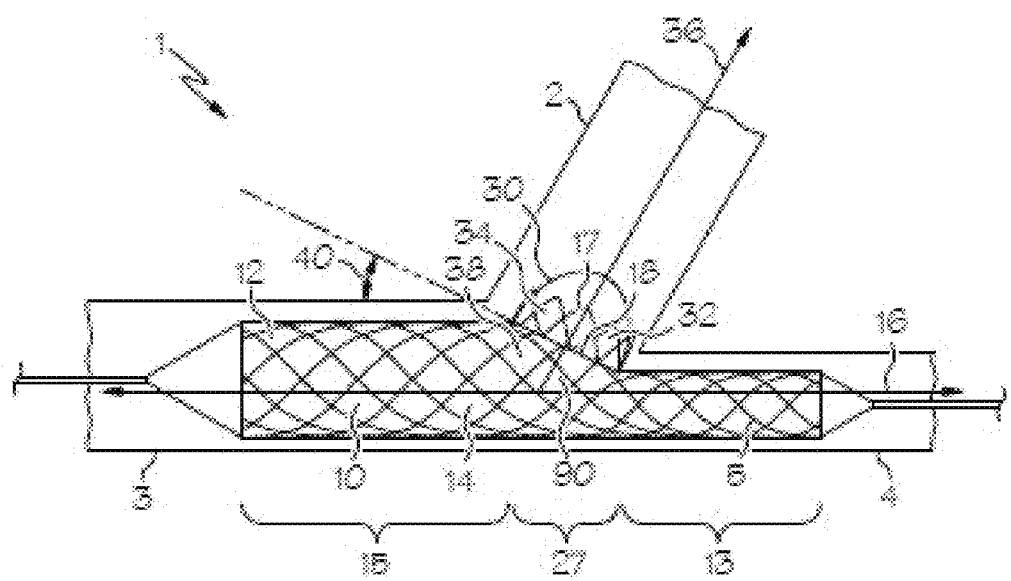
FIG. 1 is a lateral view of an expanded bifurcated stent with a larger diameter at the portion within the parent vessel and a smaller diameter at the portion within the main branch vessel.

The invention will next be illustrated with reference to the figures wherein the same numbers indicate similar elements in all figures. Such figures are intended to be illustrative rather than limiting and are included herewith to facilitate the explanation of the apparatus of the present invention.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

Referring now to FIG. 1, there is shown an expanded bifurcated stent (1). When deployed, the stent is positioned at and extends along a bifurcation site from a first or parent vessel (3) into at least two branch vessels, one being a main branch vessel (4) and one being a deviating branch vessel (2). The main branch vessel (4) generally extends along the same first longitudinal axis (16) as the parent vessel (3). The deviating branch vessel (2) generally extends along a second longitudinal axis (36). Although it would be appreciated by one of ordinary skill in the art that embodiments in which the main branch vessel extends in a direction proximal from the bifurcation site and in which the parent vessel extends in a direction distal from the bifurcation site are contemplated by this invention; for the sake of clarity, in this application the definition of the term "parent vessel" is that branch extending in a proximal direction from the bifurcation site and the definition of the term "main branch vessel" is that branch extending in a distal direction from the bifurcation site.

The inter-axis angle (90) formed at the intersection of the first longitudinal axis (16) and the second longitudinal axis (36) defines an oblique angle. For the purposes of this application, the definition of term "oblique" is an angle of greater than zero degrees, such as an angle of between about 1 and about 180 degrees and explicitly includes angles of 90 degrees and of about 90 degrees. In some bifurcated arteries, the percentage difference between the diameter of the parent vessel and the diameter of the main branch vessel is a very large and is caused by a steep tapering in the walls of the main branch vessel. In the context of this application this large tapering in body vessels is referred to as rapid percent change vessels or RPs. The tapering in RPs helps the circulatory system maintain constant fluidic barometric pressure. Examples of RP body vessels include but are not limited to the left main coronary artery, the left anterior descending (LAD) artery, and the Circumflex artery. The present invention, while generally suited to use at a wide variety of bifurcation sites in arteries, veins, and other body lumens, in some embodiments, are particularly suited for within in RP body vessels.

The bifurcated stent (1) is a hollow structure positionable adjacent to the body vessel wall. The stent (1) is typically placed on a catheter shaft and is positioned within a body vessel at the bifurcation site. The stent (1) comprises a first stent body (10), a side branch or ostial opening (18) along its surface, and a second stent body. The second stent body comprises a side branch assembly (30) adjacent to and covering at least a portion of the side branch opening (18). The inner surface of the first stent body (10) faces and defines a first fluid lumen (14). The surface of the first stent body (10) defines a first circumferential wall (12).

In the unexpanded state, the stent as a whole defines a singular tubular wall which can be substantially cylindrical or which may have regions with differing diameters or asymmetries around its longitudinal axis.

In the expanded state as shown in FIG. 1, the stent is positioned within a bifurcation site and the first stent body (10) extends from a position within the parent vessel (3) to a position within the main branch vessel (4). The second stent body comprises the expanded side branch assembly (30) which extends into the deviating branch vessel (2) and defines the second fluid lumen (34). The first stent body (10) generally extends along the first longitudinal axis (16) of the parent vessel (3) and the second stent body (30) generally extends along the second longitudinal axis (36) of the branch vessel (2).

A generally tubular portion of the first stent body (10) located at a position distal to the side branch assembly (30) defines the distal region (13). Similarly a generally tubular portion of the first stent body (10) located at a position proximal to the side branch assembly (30) defines the proximal region (15). A medial region (27) defines the portion of the first stent body (10) between the distal and proximal regions. The first and second bodies' periphery are joined at the ostium (38). The first and second bodies can be joined around the ostium (38) by connectors or by any other means known in the art. In some embodiments, a mounting ring or expandable frame can encircle the side opening providing a defined interface between the first and second bodies. In at least some embodiments, both the first and second stent bodies are formed from a single solid tube by known techniques such as laser cutting, chemical etching or the like.

The side branch assembly (30) of the second body comprises two or more projecting members (32) which extend away from the first circumferential wall (12). These extended projecting members (32) define the second fluid lumen (34). The second fluid lumen is in fluid communication with the first lumen (14).

In at least one embodiment, the projecting member (32) is a petal. For purposes of this application the definition of the term "petal" is one or more projecting members (32) capable of twisting, bending, pivoting or otherwise opening to define a second fluid lumen (34) by opening away from the circumferential layer (12) of the first stent body (10).

The petals can be arranged in an iris configuration when the stent (1) is unexpanded. For purposes of this application the definition of the term "iris" is one or more petals generally lying along the first circumferential wall (12) of the stent (1) in the unexpanded configuration and covering at least a portion of the side branch opening (18). When the stent (1) assumes an expanded state, the petals bend outward around the ostium (38) in a crown configuration to form the second fluid lumen (34). The transition from iris to crown configurations may be accomplished by balloon expansion, self-expansion or a combination of such mechanisms.

The design of the medial region (27) accommodates the severe and rapid diameter percentage decrease between the diameter of the parent vessel (3) and the main branch vessel (4) found in RP body vessels. The distal and proximal regions each have differing diameters sized to match the respective size of the parent vessel or main branch that they are positioned within. The proximal region (15) has a greater expansion capability than the distal region (13). This may be accomplished by using different materials between the stent regions or by use of different stent design features such as strut dimensions differences in undulation frequency and/or amplitude, changes in cell geometry and the like, or combinations of such differences.

The difference in diameter between the proximal and distal regions of the stent is bridged by the medial region (27) at least one embodiment of which is shown in FIG. 2 which includes several undulating expansion columns (28', 28", 28''', and 28''''), each with progressively differing expansion properties. In at least one embodiment, the expansion properties of each of the medial columns (28', 28", 28''', 28'''') progressively changes according to the formula:

$$L_{Proxiaml}/D_{Proximal} = L_{Distal}/D_{Distal}$$

In which L is the continuous length of an expansion column's undulations and D is the average target vessel diameter or nominal expansion diameter of a particular stent cross section. Medial columns conforming to this formula allow the medial column to maintain its scaffolding properties, volume for drug coatings, and maintain appropriate SAR (surface to artery ratio used for appropriate drug dosages) while allowing for the stepped decrease or gradual taper of the stent over the bifurcation. In at least one embodiment, the formula is applicable to expansion columns having undulations with common amplitudes.

One exemplary embodiment has a four column medial region where the undulations in each of the columns have equal amplitudes, the value of L for these medial columns are proportional ratios according to the relationship of: column-1 (28') L=4.0, column-2 (28") L=3.75, column-3 (28''') L=3.50, and column-4 (28'''') L=3.0. For instance, the L values for medial columns may be 4 mm, 3.75 mm, 3.5 mm, and 3 mm, respectively. In at least one embodiment, the diameter difference between the most distal and most proximal column is between 18% and 35%. The most distal of the medial columns (28'''') is attached to the distal region (13) and has the same diameter as the distal region (13). Similarly the most proximal of the medial columns (28') is attached to the proximal region (15) and has the same diameter as the proximal region (15). The intermediate medial expansion columns (which in FIG. 2 is represented by 28", 28''', but there can also be more, fewer, or none at all) provide scaffolding appropriate to particular cross sections of the rapid taper of the RP vessel or other body vessel.

The taper of the medial region as well as the body vessel can be described in terms of a slope expressed according to the common slope equation: slope=$\Delta X/\Delta Y$ wherein $\Delta X$ represents the difference in diameter at two different portions of the medial region or body vessel (63 and 64 in FIG. 9) and $\Delta Y$ represents the longitudinal displacement relative to the longitudinal axis (71 in FIGS. 9 and 10) of the different diameters. In at least one embodiment, the medial region matches an RP body vessel which decreases from a diameter of 4 mm to a diameter of 2.5 mm over a distance of approximately 6 mm resulting in a slope of 0.25. In at least one other embodiment, the diameter change is from 4 mm to 3 mm over 8 mm of distance resulting in a slope of 0.125. Embodiments of this invention contemplate but are not limited to medial regions having a length of between 10 mm and 3 mm and which have a decrease in diameter from 5 mm to 2 mm.

Although FIG. 2 illustrates a stent in which the outer surface of each of the three regions is at least partially defined by expansion columns (7) which comprise struts (5) connected to immediately adjacent struts (5') by bent regions (6) on each end of the struts (5) and in which the expansion columns (7) are connected to adjacent expansion columns (7') by connectors (37) it would be understood to one of skill in the art that the invention encompasses other stent architectures known in the art. Similarly, although FIG. 5 illustrates at least one embodiment in which there are four medial expansion columns, embodiments with two or more medial expansion columns are within the scope of this invention. In addition, the taper can be bridged by members other than medial expansion columns such as by ringed stent sections with different diameters.

Figure 3A:
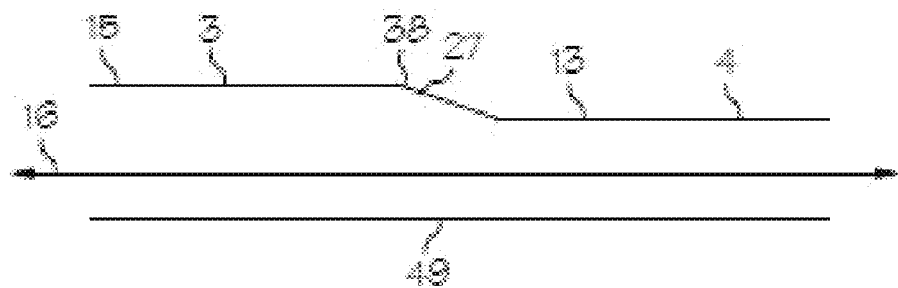
FIG. 3A is a lateral cross sectional image of a symmetrical bifurcated stent with a larger diameter at the portion within the parent vessel and a smaller diameter at the portion within the main branch vessel.
Figure 3B:
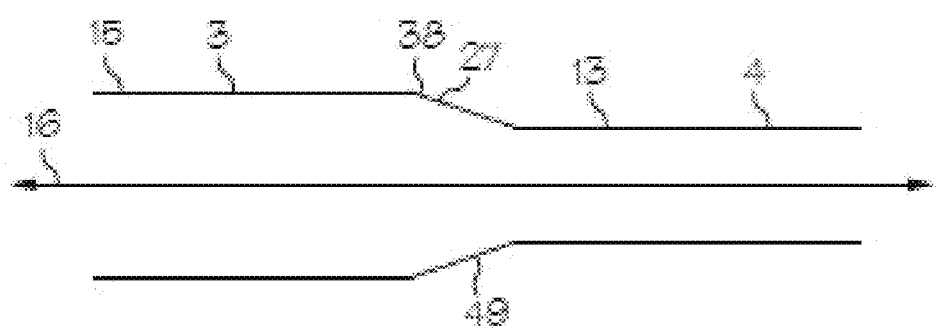
FIG. 3B is a lateral cross sectional image of an asymmetrical bifurcated stent with a larger diameter at the portion within the parent vessel and a smaller diameter at the portion within the main branch vessel.
Figure 4A:
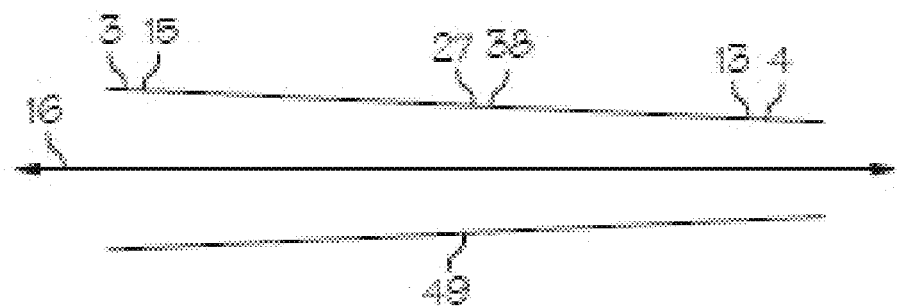
FIG. 4A is a lateral cross sectional image of a gradually tapering symmetrical bifurcated stent with a larger diameter at the portion within the parent vessel and a smaller diameter at the portion within the main branch vessel.
Figure 4B:
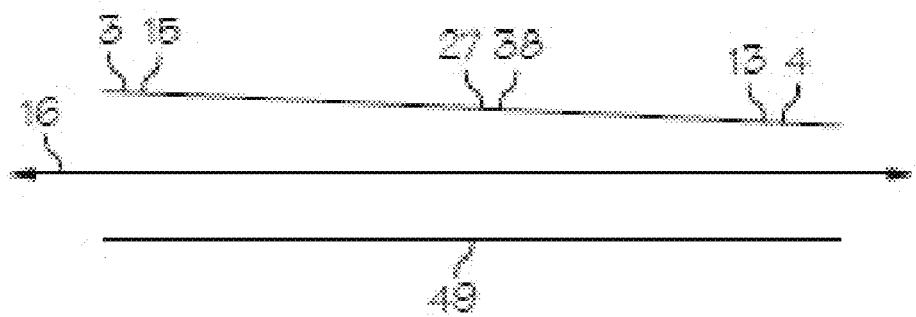
FIG. 4B is a lateral cross sectional image of a gradually tapering asymmetrical bifurcated stent with a larger diameter at the portion within the parent vessel and a smaller diameter at the portion within the main branch vessel.
Figure 5A:
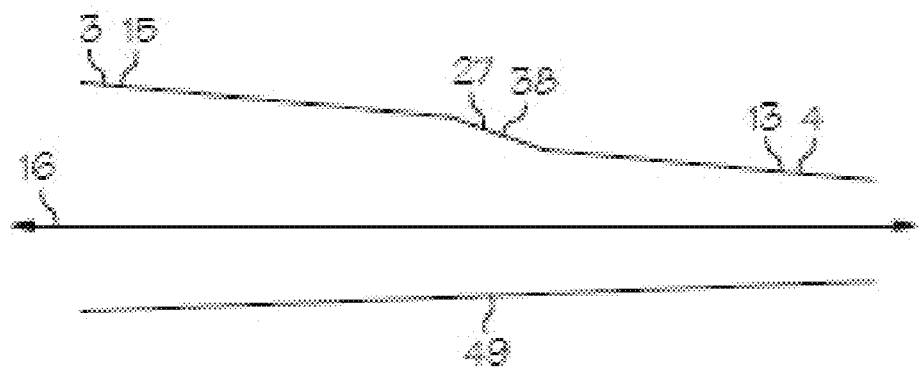
FIG. 5A is a lateral cross sectional image of a stepped tapering symmetrical bifurcated stent with a larger diameter at the portion within the parent vessel and a smaller diameter at the portion within the main branch vessel.
Figure 5B:
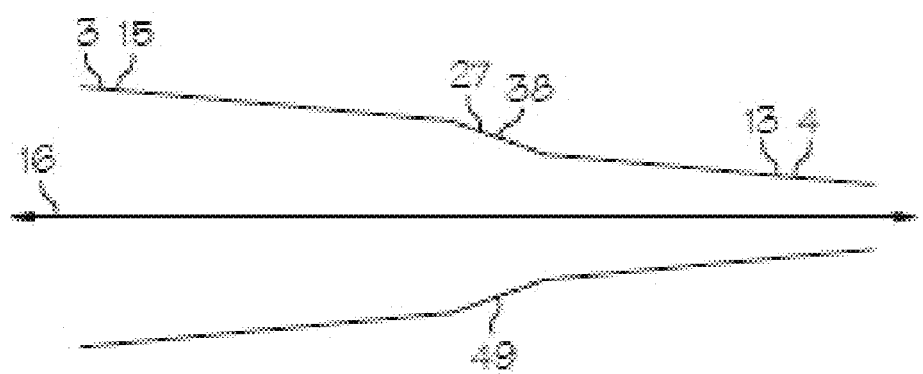
FIG. 5B is a lateral cross sectional image of a stepped tapering asymmetrical bifurcated stent with a larger diameter at the portion within the parent vessel and a smaller diameter at the portion within the main branch vessel.

Referring now to FIGS. 3A, 3B, 4A, 4B, 5A and 5B there are at least three stent configurations utilized by a bifurcated stent for an RP body vessel. Each of these configurations has an asymmetric alternative (FIGS. 3A, 4A, and 5A) and a symmetric alternative (FIGS. 3B, 4B, and 5B). In the asymmetric alternatives, the trans-ostial portion (49) of the stent (1) (the portion of the medial region (27) on the opposite side of the longitudinal axis (16) from the ostium (38)) is not a substantial coordinate reflection of the ostium (38) relative to the longitudinal axis (16). The advantage of an asymmetric alternative is that the trans-ostial portion (49) need not be expanded in an oblique direction which eases expansion, reduces the possibility of poor deployment, and reduces the possibility of barotraumas.

Along with the use of a stent (1) with non-identical expansion columns which allow for a proper fit within an RP body vessel, at least one embodiment of the invention is directed to an RP tapered balloon catheter which when expanded, matches the geometric constraints of an RP body vessel and facilitates the delivery and deployment of the stent within an RP body vessel. The method of using an RP tapered balloon catheter with a RP tapered diameter stent is within the scope of the present invention. Furthermore, an RP tapered balloon curved lengthwise to match the RP tapered diameter stent is also within the scope of the present invention. Shapes including but not limited to those disclosed in FIGS. 3A, 3B, 4A, 4B, 5A and 5B are also formed in this manner.

In at least one embodiment, using an RP tapered balloon to at least partially expand a non-RP tapered stent will also result in an RP tapered expanded stent. However, since a non-tapered stent has no change in material to compensate for the change in its surface area, such an expanded stent is RP tapered as a result of incomplete expansion. This incompletely expanded stent will therefore have increased material fraction at the main branch. For purposes of this application, material fraction is the proportion of the surface of the expanded stent covered by the stent material (such as metal). Shapes including but not limited to those disclosed in FIGS. 3A, 3B, 4A, 4B, 5A and 5B are also formed in this manner.

FIGS. 3A and 3B each illustrate a lateral stent cross section profile in which the proximal and distal sections each have a constant diameter and a stepped medial region (27) bridges between them. This design addresses the rapid taper that can occur in RP vessels where the proximal and distal regions themselves are non-tapered. FIGS. 4A and 4B illustrate lateral stent cross section profiles in which there is a gradual taper extending completely from the proximal region through the medial region (27) to the distal region. This design is particularly suited for body vessels in which the proximal and distal regions themselves are tapered and do not have a large change in diameter between the parent vessel and the main branch. FIGS. 5A and 5B illustrate profiles that accommodate tapers present in the parent vessel and the main branch as well as being suited for a rapid decrease in diameter between the parent vessel and the main branch.

Figure 6:
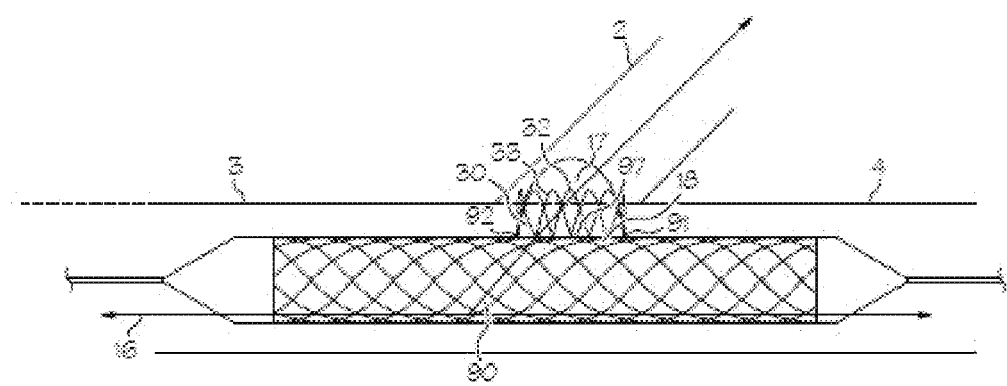
FIG. 6 is a PRIOR ART bifurcated stent.

A comparison of the stent in FIG. 1 with the PRIOR ART stent of FIG. 6 is useful to appreciate some embodiments of the invention. When compared with the PRIOR ART stent of FIG. 6 it can be appreciated that tapered stent of FIG. 1 accommodates a rapid decrease in diameter between the parent vessel and the main branch. In addition, the sloped medial region (27) in the stent of FIG. 1 orients the side branch assembly (30) along an ostial angle (40) and within a branching plane (43) which allows the projecting members or petals (32) to extend substantially along the second longitudinal axis (36). That portion of the side opening (18) that lies along the branching plane (43) is the opening plane.

Referring again to FIG. 1 there is shown another attribute of the stent that the ostial angle (40) that the branching plane (43) forms with the first longitudinal axis (16) greatly facilitates the crowning of the side branch assembly (40). The fact that the entire ostial region is angled along a common branching plane (43) reduces the physical requirements of the projecting members or petal members (32) of the side branch assembly (30) to define a lumen at the same oblique angle.

The stent of FIG. 1 also provides more side stent coverage than the PRIOR ART stent of FIG. 6. In both stents, a plurality of ostial engagement points (97) at the point of engagement between the extended side branch assembly (30) and the first stent body (10) encircle the ostium (38). In the PRIOR ART stent of FIG. 6, when the second lumen is extended along the inter-axis angle (90) at a non-ninety degree angle, one ostial engagement point (97) is a most acute side angle or acute carina (91), one ostial engagement point (97) will be at a most obtuse side angle or obtuse carina (92), and the remainder of ostial engagement points (97) will be at one or more intermediate angles of increasing acuteness relative to their proximity to the most acute carina (91). There is a direct correlation between the acuteness of an ostial engagement point's angle and the axial stress imposed on the ostial engagement point (97) when the projecting member(s) (such as petals) (33) of the side branch assembly (30) are in a crown configuration. In the stent of FIG. 1 however, the medial region pivots the ostium as a whole along the branching plane (43) assuring that all of the ostial engagement points (97) bend along a common plane and undergo similar levels of stress. This common level of stress removes the need to selectively reinforce or weaken particular ostial engagement points (97) relative to the degree to which they bend, flex, or pivot when assuming a crown configuration.

In at least one embodiment, the stent of FIG. 1 has projecting members (33) of equal length. The significance of these equally long projecting members (33) can better be understood by their comparison with the PRIOR ART stent of FIG. 6. In the PRIOR ART stent of FIG. 6, if it is desirable to have the second fluid lumen terminus (17) be generally uniformly at a right angle to the second longitudinal axis (36), the most acute ostial engagement point (91) must be closer to the second fluid lumen terminus (17) than the other ostial engagement points (97) are. Similarly, the most obtuse ostial engagement point (92) must be farther from the terminus than the other ostial engagement points (97). This is because in the PRIOR ART stent design of FIG. 6, either the various projecting members (32) must have differing lengths or a terminus (17) with a non-perpendicular angle and with a non-uniform angle to the second longitudinal axis (36) will result.

The bifurcated stent of FIG. 1 is particularly suited to provide a terminus (17) that is generally uniformly at a right angle to the second longitudinal axis (36). FIG. 1 shows that although the projecting members (33) can all have a common uniform length regardless of the inter-axis angle (90) they still form a terminus (17) with a generally uniform circumference. Similarly in at least one embodiment of the stent of FIG. 1, the projecting members (32) all have a common uniform length regardless of the inter-axis angle (90) and form a terminus (17) with a generally perpendicular circumference relative to the second longitudinal axis (36). In at least one embodiment, each of the projecting members (33) are equally wide. In at least one embodiment, each of the projecting members (33) are equally thick.

The stent (1) can be constructed according to a number of possible designs. In at least one embodiment, the tubular structure of the distal and proximal regions of the stent (1) includes a plurality of interconnected expansion struts (5) which form expansion columns (7). The struts of various expansion columns (7) can be interconnected by connector struts (37). The open areas bordered by the various expansion columns (7) and connectors (37) define a plurality of cells (11). The first stent body (10) has at least one diameter having a first magnitude which permits intraluminal delivery of the tubular structure into the body vessel passageway, and is expanded and/or deformed to achieve upon the application of a radially, outwardly extending force to form diameters which substantially match the contours of an RP body vessel. In at least one embodiment, in the unexpanded state the stent as a whole has a generally uniform diameter and in the expanded state the proximal distal and medial regions assume their different expanded diameters (8). The side opening and the second lumen can be any number of shapes including but not limited to rectangular, square, circular, elliptical, or combination thereof. In at least one embodiment the cells (11) are smaller than the side branch opening (18).

Figure 7:
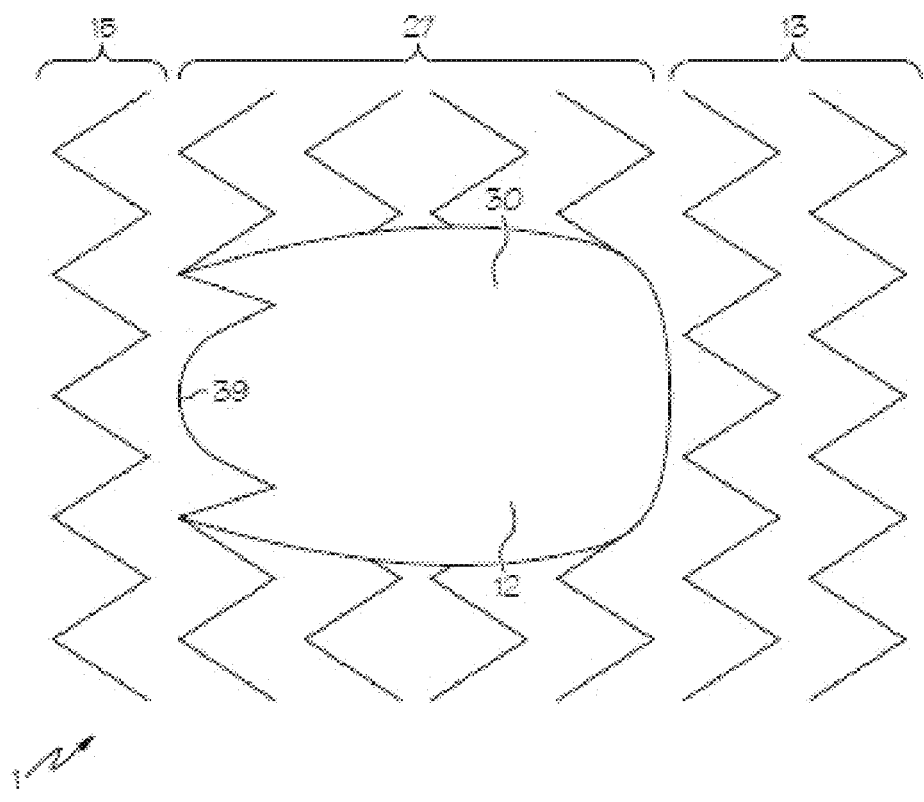
FIG. 7 is an overhead view of the side branch assembly of a bifurcated stent with a larger diameter at the portion within the parent vessel and a smaller diameter at the portion within the main branch vessel.
Figure 8:
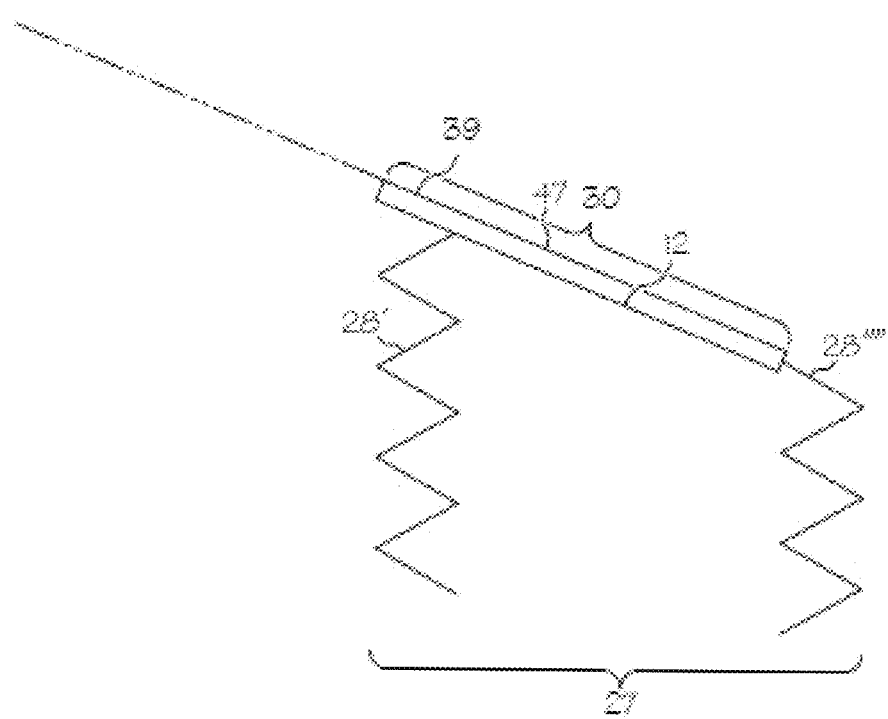
FIG. 8 is a cross sectional view of the side branch assembly of a bifurcated stent with a larger diameter at the portion within the parent vessel and a smaller diameter at the portion within the main branch vessel.

As is shown in FIGS. 7 and 8, at least a portion of the base of the side branch assembly (30) is an expandable frame (47). Examples of expandable frames are disclosed in the commonly owned co-pending application 60/859,420 having an attorney docket number of S63.2-13226-US01 which has a title of "Bifurcation Stent Design with Over Expansion Capability" which is hereby incorporated by reference in its entirety. As shown in FIG. 7, in the unexpanded state, the expandable frame (47) has a generally looped structure about at least a portion of the side opening with one or more curved regions or additional nested peaks (39) lying along the first circumferential wall (12). The nested peaks depicted in FIG. 7 comprise a first ascending segment (39'), a second descending segment (39"), a third ascending segment (39'''), a fourth descending segment (39''''), a fifth ascending segment (39'''''), and a sixth descending segment (39''''''). While FIG. 7 illustrates a nested peak configuration having six segments, embodiments with more or fewer segments are contemplated by the invention.

The nested peaks (39) when in the unexpanded state reduce the overall area of the circumferential wall (12) that the base of the side branch assembly (30) occupies when the stent is in the unexpanded configuration. When the expandable frame (47) is expanded as shown in FIG. 8, the additional nested peaks (39) expand along the branching plane (43) in a direction co-linear to the opening plane and with the remainder of the base of the side branch array (30). For purposes of this application the term "co-linear" defines a relationship of elements where all of the elements are in a common linear order relative to a single axis. This expansion increases the area of the base the side branch assembly (30) crowns away from. The expandable frame (47) allows for greater amount of scaffolding support for the side branch assembly (30) without impinging on the stent's overall performance or its ability to be crimped into a size appropriate for implantation. Petals or other projecting members can be engaged to the nested peak (39) allowing the second stent body to define a second fluid lumen with a greater volume.

In one embodiment of this invention, the expanded nested peak of FIG. 8 is completely extended to form a substantially rounded side branch assembly base. In another embodiment of this invention, the nested peaks only partially expand to result in an expanded side branch assembly base which still retains some peaked structures. In another embodiment of this invention, two or more nested peaks are present on the side branch assembly.

Figure 9:
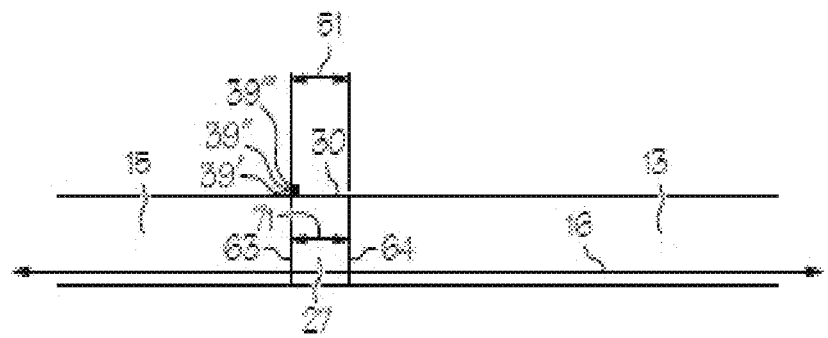
FIG. 9 is representational view of the side branch assembly of an unexpanded bifurcated stent with an expandable frame array.
Figure 10:
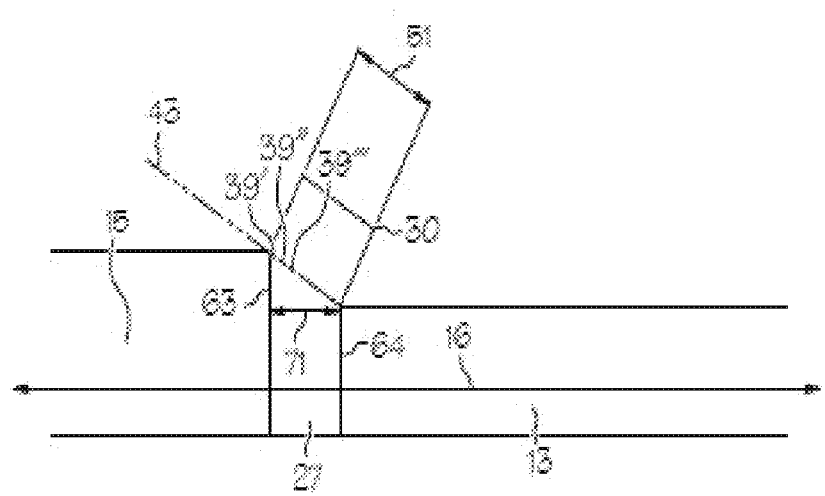
FIG. 10 is representational view of the side branch assembly of an expanded bifurcated stent with an expandable frame array.

In at least one embodiment the expandable frame (47) facilitates the increase in length that the side branch assembly spans when the stent is expanded. A comparison of schematic FIGS. 9 and 10 show that the base of the side branch assembly (30) when unexpanded as shown in FIG. 9, has a longitudinal length (71) running parallel to the longitudinal axis (16) which is equal to the sloped length (51) (the length measured according to the slope of the side branch assembly base (30)). FIG. 10 however illustrates that the diagonal slope length (51) becomes larger than the longitudinal length (71) when the stent is expanded. FIG. 9 shows that the ascending and descending segments (39', 39", 39''') occupy similar or overlapping longitudinal positions when unexpanded. It should be understood that FIG. 9 is a schematic drawing and the segments are positioned only to demonstrate their longitudinal offsets, they are not in fact layered on top of each other but are alongside each other as illustrated in FIG. 8. FIG. 10 illustrates that when expanded, at least some of the segments (39', 39", and 39''') have longitudinally offset positions from each other which increases the length of the side branch assembly base and help it to span the increased distance.

One embodiment can be appreciated by a comparison of FIG. 2 with FIG. 8. In FIG. 2, when expanded, the bent region (6) of the endmost expansion column in the medial region extends substantially past and out from under the base of the side branch assembly relative to the longitudinal axis. In contrast, in FIG. 8 the expanded descending segments (39) extend the base farther which in turn causes the strut's bent regions to be positioned below or at least less distant from the extending segments (39). Such positioning avoids crowding portions of the medial region against the distal or proximal regions and provides extra space for fitting longer struts, longer bent regions, or any other stent member.

In some embodiments the stent, its delivery system, or other portion of an assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

The therapeutic agent can be at least one or various types of therapeutic agents including but not limited to: at least one restenosis inhibiting agent that comprises drug, polymer and bio-engineered materials or any combination thereof. In addition, the coating can be a therapeutic agent such as at least one drug, or at least one other pharmaceutical product such as non-genetic agents, genetic agents, cellular material, etc. Some examples of suitable non-genetic therapeutic agents include but are not limited to: at least one anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate. It will be appreciated that other types of coating substances, well known to those skilled in the art, can be applied to the stent (1) as well.

This completes the description of the preferred and alternate embodiments of the invention. The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

The invention claimed is:

1. A bifurcated stent having an unexpanded state and an expanded state, the stent constructed of a plurality of interconnected strut members forming a plurality of expansion columns along a length of the stent, the stent comprising:
a generally tubular first body defining a first lumen, the first body having a side opening bounded by a perimeter, a distal region distal to the side opening and having a distal region diameter, a proximal region proximal to the side opening and having a proximal region diameter, and a medial region between the distal and proximal regions, wherein the medial region defines the side opening,
wherein the medial region comprises at least three axially spaced expansion columns, each expansion column has a plurality of undulations, a continuous length including the undulations, and a diameter, the at least three axially spaced expansion columns comprise a proximal most expansion column at a proximal end of the medial region, a distal most expansion column at a distal end of the medial region, and at least one intermediate expansion column therebetween, wherein the proximal most expansion column and the distal most expansion column have different maximum expansion capacities, wherein the continuous length of the proximal most expansion column of the medial region is greater than the continuous length of the at least one intermediate expansion column, and the continuous length of the at least one intermediate expansion column is greater than the continuous length of the distal most expansion column of the medial region;
wherein, in the expanded state, the proximal region diameter is greater than the distal region diameter, wherein the proximal region diameter and the distal region diameter differ in size by one magnitude selected from the inclusive range of 18% to 35%;
wherein the medial region has a tapering diameter transitioning from a maximum diameter equal to the proximal region diameter at a proximal end of the medial region to a minimum diameter equal to the distal region diameter size at a distal end of the medial region, and
a second body comprising at least two projecting members, wherein, in the expanded state, at least one of the projecting members of the second body extends obliquely from the first body, and the projecting members define a second lumen therethrough, and the second lumen is in fluid communication with the first lumen.

2. The stent of claim 1 in which the first body comprises a plurality of interconnected strut members, and a plurality of cells defining open spaces in the first lumen between interconnected strut members, the interconnected members being connected by at least one connector, the cells being in fluid communication with the first lumen and having an area greater than that of the side opening.

3. The stent of claim 2 further comprising at least one therapeutic agent coating, the at least one therapeutic agent coating being positioned at one location selected from the group consisting of: at least one connector, at least one stent member, at least one projecting member, the distal region, the proximal region, the medial region, the first stent body, the second stent body, and any combination thereof.

4. The stent of claim 1 in which there are four interconnected expansion columns in the medial region.

5. The stent of claim 1 in which at least a portion of the distal region and at least a portion of the proximal region have a common axis.

6. The stent of claim 1, wherein the projecting members commonly extend around an axis oblique to the generally tubular first body, each projecting member has an outermost tip at a location farthest from the generally tubular first body, each outermost tip is spaced such that an axis extending between any two outermost tips is substantially perpendicular to the axis oblique to the generally tubular first body.

7. The stent of claim 1, wherein the undulations of the expansion columns of the medial region have equal amplitudes.

8. The stent of claim 1, wherein each expansion column of the medial region has a ratio of continuous length to diameter, wherein the ratio for the proximal most expansion column of the medial region is equal to the ratio for the distal most expansion column of the medial region.

9. The stent of claim 1, wherein the proximal region has a greater expansion capacity than the distal region.

10. A bifurcated stent comprising:
a generally tubular first body defining a first lumen, the first body having a side opening bounded by a perimeter, a distal region distal to the side opening and having a diameter, a proximal region proximal to the side opening and having a diameter, and a medial region between the distal and proximal regions, wherein the medial region defines the side opening,
wherein the medial region comprises four axially spaced expansion columns,
wherein each expansion column of the medial region has a plurality of undulations, a continuous length including the undulations, and a diameter,
wherein, from a proximal end to a distal end of the medial region, the four axially spaced expansion columns of the medial region comprise a first expansion column, a second expansion column, a third expansion column, and a fourth expansion column, wherein the first expansion column and the fourth expansion column have different maximum expansion capacities, wherein the continuous length of the first expansion column is greater than the continuous length of the second expansion column, and the continuous length of the second expansion column is greater than the continuous length of the fourth expansion column of the medial region;
wherein the distal region diameter and proximal region diameter of the first body have different sizes, the proximal region diameter size being greater than the distal region diameter size, the medial region has a tapering diameter transitioning from a maximum diameter equal to the proximal region diameter size at a proximal end of the medial region to a minimum diameter equal to the distal region diameter size at a distal end of the medial region, and
a second body comprising at least two projecting members, wherein, in an expanded state, at least one of the projecting members of the second body extends obliquely from the first body, and the projecting members define a second lumen therethrough, and the second lumen is in fluid communication with the first lumen.

11. The stent of claim 10, wherein the continuous length of the second expansion column is greater than the continuous length of the third expansion column of the medial region, and the continuous length of the third expansion column of the medial region is greater than the continuous length of the fourth expansion column of the medial region.

12. The stent of claim 10, wherein each expansion column comprises a plurality of interconnected struts.

13. The stent of claim 10, wherein the undulations of the expansion columns of the medial region have equal amplitudes.

14. The stent of claim 10, wherein each expansion column of the medial region has a ratio of continuous length to diameter, wherein the ratio for the proximal most expansion column of the medial region is equal to the ratio for the distal most expansion column of the medial region.

15. The stent of claim 10, wherein the proximal region has a greater expansion capacity than the distal region.

* * * * *